(12) United States Patent
Trenholm et al.

(10) Patent No.: US 11,029,141 B2
(45) Date of Patent: Jun. 8, 2021

(54) ANTICIPATORY DEPTH OF FIELD ADJUSTMENT FOR OPTICAL COHERENCE TOMOGRAPHY

(71) Applicant: SIGHTLINE INNOVATION INC., Toronto (CA)

(72) Inventors: Wallace Trenholm, Toronto (CA); Lorenzo Pons, Toronto (CA)

(73) Assignee: SIGHTLINE INNOVATION INC., Toronto (CA)

( * ) Notice: Subject to any disclaimer, the term of this patent is extended or adjusted under 35 U.S.C. 154(b) by 0 days.

(21) Appl. No.: 16/460,628

(22) Filed: Jul. 2, 2019

(65) Prior Publication Data

US 2020/0003543 A1 Jan. 2, 2020

Related U.S. Application Data

(63) Continuation of application No. 16/006,022, filed on Jun. 12, 2018, now Pat. No. 10,386,172.

(60) Provisional application No. 62/518,206, filed on Jun. 12, 2017.

(51) Int. Cl.
*G01B 9/02* (2006.01)
*G01N 21/95* (2006.01)
*A61B 5/00* (2006.01)
*G01N 21/88* (2006.01)
*G01N 21/47* (2006.01)

(52) U.S. Cl.
CPC ............ *G01B 9/02035* (2013.01); *A61B 5/00* (2013.01); *A61B 5/0066* (2013.01); *A61B 5/6844* (2013.01); *G01B 9/02063* (2013.01); *G01B 9/02091* (2013.01); *G01N 21/4795* (2013.01); *G01N 21/8806* (2013.01); *G01N 21/95* (2013.01)

(58) Field of Classification Search
CPC ............ G01B 9/02035; G01B 9/02091; G01B 9/02063; G01B 9/02064; G01B 9/02065; G01B 9/02029; G01N 21/4795; G01N 21/95; G01N 21/8806
See application file for complete search history.

(56) References Cited

U.S. PATENT DOCUMENTS

| 2006/0170930 A1* | 8/2006 | Li | A61B 5/0059 356/479 |
| 2013/0188139 A1* | 7/2013 | Sato | A61B 3/102 351/206 |
| 2016/0007847 A1* | 1/2016 | Dziubak | A61B 3/102 351/206 |

* cited by examiner

*Primary Examiner* — Tarifur R Chowdhury
*Assistant Examiner* — Jonathon Cook
(74) *Attorney, Agent, or Firm* — Bhole IP Law; Anil Bhole; Marc Lampert

(57) ABSTRACT

A system and method for surface inspection of an object using optical coherence tomography (OCT) with anticipatory depth of field adjustment is provided. The method includes determining a present working distance and one or more forward working distances; determining a present depth of field in which the surface of the object is in focus at the location of the present working distance and at as many of the consecutive forward surface locations as determined possible; changing to the present depth of field; performing an A-scan of the object; moving the object such that the scanner head is directed at each of the consecutive forward surface locations determined to be in the present depth of field; and performing an A-scan at each of the consecutive forward surface locations determined to be in the present depth of field.

16 Claims, 16 Drawing Sheets

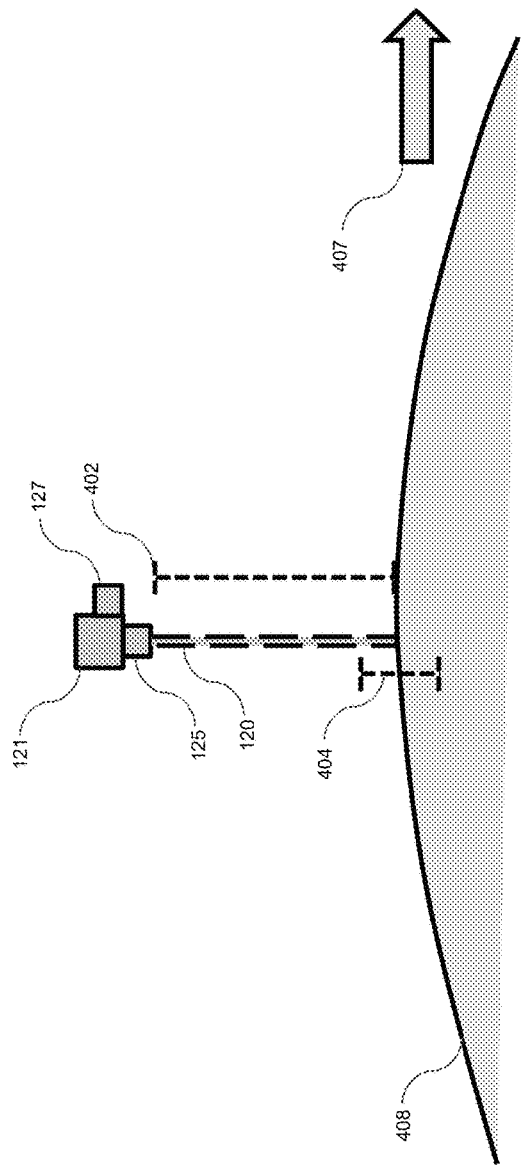
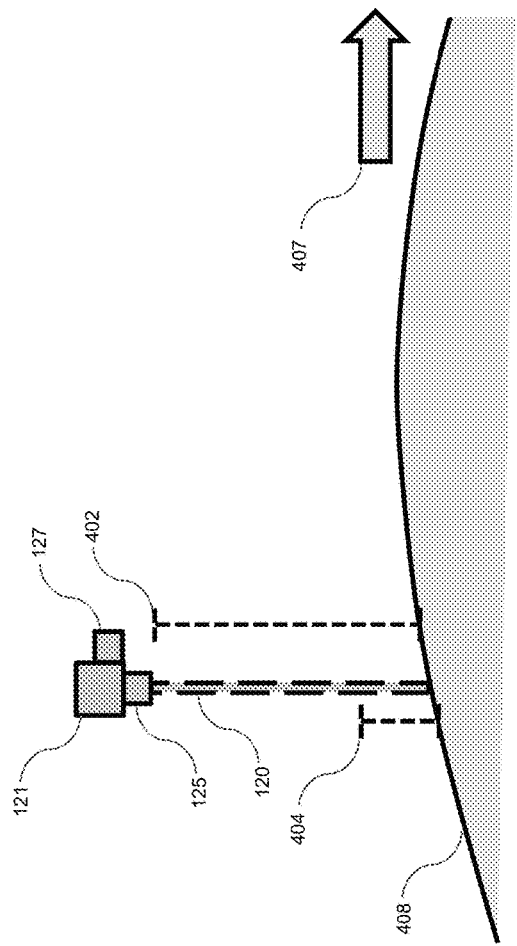

ANTICIPATORY DEPTH OF FIELD ADJUSTMENT FOR OPTICAL COHERENCE TOMOGRAPHY

TECHNICAL FIELD

The following relates generally to imaging and more specifically to a system and method for anticipatory depth of field adjustment for optical coherence tomography.

BACKGROUND

In many applications, imaging can be used to garner information about a particular object; particularly aspects about its surface or subsurface. One such imaging technique is tomography. A device practicing tomography images an object by sections or sectioning, through the use of a penetrating wave. Conventionally, tomography can be used for various applications; for example, radiology, biology, materials science, manufacturing, quality assurance, quality control, or the like. Some types of tomography include, for example, optical coherence tomography, x-ray tomography, positron emission tomography, optical projection tomography, or the like.

Conventionally, the above types of tomography, and especially optical coherence tomography, produce detailed imaging of an object; however, inaccuracies and problems can arise with respect to properly imaging the object.

SUMMARY

In an aspect, there is provided a method of surface inspection of a moveable object using optical coherence tomography (OCT), the method comprising: determining a first working distance between a scanner head and a first surface location on the object; determining one or more forward working distances located along the object, opposite a direction of travel of the object, from the first surface location, each forward working distance is a distance between the scanner head and a respective forward surface location on the object; determining a present depth of field, based on the first working distance and the one or more forward working distances, where the surface of the object is within the present depth of field at the present surface location and at as many of the consecutive forward surface locations as determined possible; changing a current depth of field to the present depth of field; performing an A-scan of the object at the present surface location; moving the object along the direction of travel such that the scanner head is directed at each of the consecutive forward surface locations determined to be in the present depth of field; and performing an A-scan at each of the consecutive forward surface locations determined to be in the present depth of field.

In a particular case, after moving the object to a last of the consecutive forward surface locations determined to be in the present depth of field, the method further comprising: determining one or more subsequent forward working distances located at subsequent forward surface locations along the object, opposite the direction of travel of the object, from the present surface location; determining the present depth of field, based on the forward working distance at the present surface location and the one or more subsequent forward working distances, where the surface of the object is within the present depth of field at the present surface location and at as many of the consecutive subsequent forward surface locations as determined possible; changing the current depth of field to the present depth of field; performing an A-scan of the object at the present surface location; moving the object along the direction of travel such that the scanner head is directed at each of the consecutive subsequent forward surface locations determined to be in the present depth of field; and performing an A-scan at each of the consecutive subsequent forward surface locations determined to be in the present depth of field.

In another case, at least a portion of the object has a curved surface profile.

In yet another case, determining the first working distance, determining the one or more forward working distances, and determining the subsequent forward working distances each comprise measuring a distance between the scanner head and the surface of the object.

In yet another case, the method further comprising retrieving a surface geometry of the object from a database, and determining the first working distance, determining the one or more forward working distances, and determining the subsequent forward working distances each comprise determining a distance between the scanner head and the surface of the object from the surface geometry of the object.

In yet another case, at least some of the A-scans are aggregated together into a B-scan.

In yet another case, moving the object along the direction of travel comprises continuously moving the object.

In yet another case, the one or more forward working distances and the one or more subsequent forward working distances are predetermined.

In yet another case, using the A-scans data, the method further comprising detecting a feature on a surface or subsurface of the object using a neural network trained using a training set, the training set comprising A-scans data with a known feature.

In yet another case, the neural network comprises a long short-term memory (LSTM) machine learning approach and a convolutional neural network machine learning approach.

In yet another case, the method further comprising detecting a location of the detected feature using the neural network.

In another aspect, there is provided a system for surface inspection of a moveable object using an optical coherence tomography (OCT) system, the OCT system comprising an optical source to produce an optical beam, a beam splitter to direct derivatives of the optical beam to a reflective element and the object and direct optical beams returned from the reflective element and the object to a detector for detection of an interference effect, the system for surface inspection comprising: a distance determination module to determine a first working distance between a scanner head of the OCT system and a first surface location on the object, and to determine one or more forward working distances located along the object, opposite a direction of travel of the object, from the first surface location, each forward working distance is a distance between the scanner head and a respective forward surface location on the object; a depth-of-field module to determine a present depth of field, based on the first working distance and the one or more forward working distances, where the surface of the object is within the present depth of field at the present surface location and at as many of the consecutive forward surface locations as determined possible; a depth-of-field adjusting mechanism to change a current depth of field to the present depth of field, the OCT system performing and outputting an A-scan of the object at the present surface location; and an object translator to move the object along the direction of travel such that the scanner head is directed at each of the consecutive forward surface locations determined to be in the present depth of field, the OCT system performing an A-scan at each of the consecutive forward surface locations determined to be in the present depth of field.

In a particular case, after the object translator moves the object to a last of the consecutive forward surface locations determined to be in the present depth of field: the distance determination module determines one or more subsequent forward working distances located at subsequent forward surface locations along the object, opposite the direction of travel of the object, from the present surface location; the depth-of-field module determines the present depth of field, based on the forward working distance at the present surface location and the one or more subsequent forward working distances, where the surface of the object is within the present depth of field at the present surface location and at as many of the consecutive subsequent forward surface locations as determined possible; the depth-of-field adjusting mechanism changes the current depth of field to the present depth of field, the OCT system performing and outputting an A-scan of the object at the present surface location; the object translator moves the object along the direction of travel such that the scanner head is directed at each of the consecutive subsequent forward surface locations determined to be in the present depth of field, the OCT system performing an A-scan at each of the consecutive subsequent forward surface locations determined to be in the present depth of field.

In another case, at least a portion of the object has a curved surface profile.

In yet another case, the distance determination module determines the first working distance, the one or more forward working distances, and the subsequent forward working distances by measuring a distance between the scanner head and the surface of the object.

In yet another case, the distance determination module retrieves a surface geometry of the object from a database and the distance determination module determines the first working distance, the one or more forward working distances, and the subsequent forward working distances by determining a distance between the scanner head and the surface of the object from the surface geometry of the object.

In yet another case, the object translator moves the object along the direction of travel by continuously moving the object.

In yet another case, the object translator stops moving the object prior to the performing of the A-scan at the present surface location, at each of the forward surface locations, and at each of the subsequent forward surface locations.

In yet another case, the direction of travel of the object can be along a two-dimensional plane.

These and other aspects are contemplated and described herein. It will be appreciated that the foregoing summary sets out representative aspects of systems and methods to assist skilled readers in understanding the following detailed description.

BRIEF DESCRIPTION OF THE DRAWINGS

The features of the invention will become more apparent in the following detailed description in which reference is made to the appended drawings wherein:

FIG. 4A is a diagrammatic side view of a scanner head and object, according to the system of FIG. 1;

FIG. 4B is a diagrammatic side view of the scanner head and object of FIG. 4A at a later point in time;

DETAILED DESCRIPTION

Figure 1:
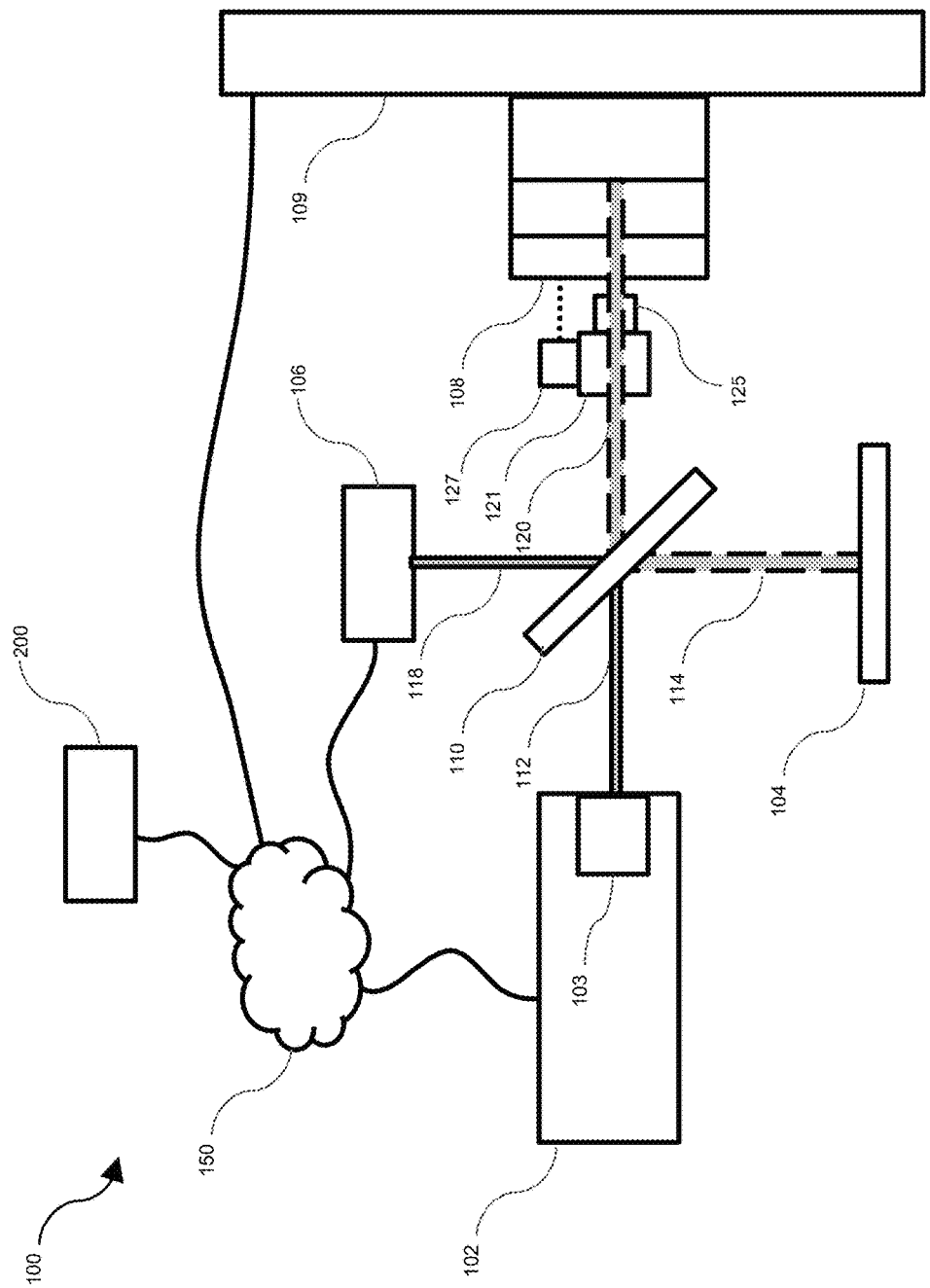
FIG. 1 is a schematic diagram of an optical coherence tomography (OCT) system, according to an embodiment.

Embodiments will now be described with reference to the figures. For simplicity and clarity of illustration, where considered appropriate, reference numerals may be repeated among the Figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

Various terms used throughout the present description may be read and understood as follows, unless the context indicates otherwise: "or" as used throughout is inclusive, as though written "and/or"; singular articles and pronouns as used throughout include their plural forms, and vice versa; similarly, gendered pronouns include their counterpart pronouns so that pronouns should not be understood as limiting anything described herein to use, implementation, performance, etc. by a single gender; "exemplary" should be understood as "illustrative" or "exemplifying" and not necessarily as "preferred" over other embodiments. Further definitions for terms may be set out herein; these may apply to prior and subsequent instances of those terms, as will be understood from a reading of the present description.

Any module, unit, component, server, computer, terminal, engine or device exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the device or accessible or connectable thereto. Further, unless the context clearly indicates otherwise, any processor or controller set out herein may be implemented as a singular processor or as a plurality of processors. The plurality of processors may be arrayed or distributed, and any processing function referred to herein may be carried out by one or by a plurality of processors, even though a single processor may be exemplified. Any method, application or module herein described may be implemented using computer readable/executable instructions that may be stored or otherwise held by such computer readable media and executed by the one or more processors.

The following relates generally to imaging and more specifically to a system and method for anticipatory depth of field adjustment for optical coherence tomography.

Optical coherence tomography (OCT), and particularly non-destructive OCT, is a technique for imaging in two or three-dimensions. OCT can provide a relatively high resolution, potentially up to few micrometers, and can have relatively deep penetration, potentially up to a few millimeters, in a scattering media.

OCT techniques can use back-scattered light from an object to generate information about that object; for example, generating a three-dimensional representation of that object when different regions of the object are imaged.

FIG. 1 illustrates a schematic diagram of an OCT system 100, according to an embodiment. The OCT system 100 includes an optical source (or photonic emitter) 102, a reflective element 104 (for example, a mirror), a beam splitter 110, and a detector (for example, a photodetector) 106. The diagram shows an object 108 with three layers of depth. The optical source 102 produces an originating optical beam (or path) 112 that is directed towards the beam splitter 110. The beam splitter 110 divides the originating beam 112 and directs one derivative beam (or path) 114 towards the reflective element 104 and another derivative beam, referred to herein as the sample beam (or path) 120, towards the object to be scanned 108. Both derivative beams 114, 120 are directed back to the beam splitter 110, and then directed as a resultant beam 118 to the detector 106. In some cases, one or more secondary mirrors (not shown) can be provided to reflect the sample beam 120 onto the object 108. In some cases, there may be a scanner head 121 to direct the sample beam 120 onto the object 108. In some cases, the scanner head 121 can include a beam steering device to direct light to the object 108. The beam steering device may be, for example, a mirror galvanometer in one or two dimensions, a single axis scanner, a microelectromechanical system (MEMs)-based scanning mechanism, a rotating scanner, or other suitable mechanism for beam steering. The beam steering device may be controlled electromechanically. In some embodiments, as described herein, the scanner head 121 can include a depth-of-field adjusting mechanism 125.

In some cases, the OCT system 100 can include a distance determination module 127 for determining the distance between the scanner head and the object 108. In an example, the distance determination module 127 can be an infrared line scanner, laser rangefinder, 3D laser scanner, radar based rangefinder, or the like. In some cases, the distance determination module 127 may be associated with, or separate from, the scanner head 121.

In some cases, the system 100 can include an amplification mechanism; for example, a doped fiber amplifier, a semiconductor amplifier, a Raman amplifier, a parametric amplifier, or the like. The amplification mechanism can be used to amplify the signal of the optical source 102 and/or to increase quantity of photons backscattered off the surface under inspection and collected on the detector 106. By using the amplification mechanism, sensitivity of the system 100 may be increased.

In some cases, the system 100 can include an object translator 109 to move the object relative to the sample beam 120 and/or the scanner head 121. The object translator 109 can be, for example, a conveyor system, a robotic system, or the like. The illustration of FIG. 1 is only diagrammatic as the optical paths can be comprised of optical cables, and as such, the system components can have any number of physical placements and arrangements.

The optical source 102 can be any light source suitable for use with an interferometric imaging modality; for example, a laser or light emitting diode (LED). Particularly, in some implementations, the optical source 102 can be a tunable laser the wavelength of which can be altered (i.e. swept) in a controlled manner; for example, to sweep a wide wavelength range (e.g. 110 nm) at high speed (e.g. 20 KHz). In a particular example, the tunable laser can have a centre wavelength of 1310 nm, wherein the wavelength of the emitted light is continuously scanned over a 110 nm range, with a scan rate of 20 kHz and a coherence length of over 10 mm. In a further embodiment, the optical source 102 may be a low coherence light source such as white light or an LED. As an example, using a low coherence light source can facilitate extraction of spectral information from the imaging data by distributing different optical frequencies onto a detector array (e.g. line array CCD) via a dispersive element, such as a prism, grating, or other suitable device. This can occur in a single exposure as information of the full depth scan can be acquired.

In some cases, the optical source 102 can include a collimator 103 for narrowing the originating beam 112. In further cases, further optics may be included in various stages of the system 100 to control or change the optical beams. Optics may include lenses or other optical devices suitable to control, guide, navigate, position, or the like, the light beam in a desired manner; as an example, an F-theta or telecentric lens may be included. Where an F-theta or telecentric lens is used, the planification means that the depth-of-field adjusting mechanism 125 only has to compensate in the axial direction, along the z-axis of the optical beam, as described below.

In further cases, software techniques may be employed for correcting or affecting optical errors or signals.

The detector 106 can be any suitable photodetector. In a particular case, the detector 106 can be a balanced photodetector, which can have an increased signal to noise ratio. In further cases, the detector 106 may be a photoelectric-type photodetector, such as a charge-coupled device (CCD) or complementary metal-oxide semiconductor (CMOS). The detector 106 may operate by photoemission, photovoltaic, thermal, photochemical, or polarization mechanism, or other mechanism through which electromagnetic energy can be converted into an electrical signal. Upon receiving the resultant beam 118, the detector 106 can convert the radiance/intensity of the resultant beam 118 into an electrical signal. In some cases, the electrical signal may then be converted to a digital signal, and modified by signal conditioning techniques such as filtering and amplification. In some cases, the interference pattern corresponding to the backscattered light can be converted into a signal by the detector 106 via, for example, a high-speed digitizer.

The OCT system also includes a computing module 200. The computing module 200 may be locally communicatively linked or remotely communicatively linked, for example via a network 150, to one or more other elements of the system 100; for example, to the optical source 102, the detector 106, the object translator 109, the scanner head 121, the depth-of-field adjusting mechanism 125, and the distance determination module 127. The computing module 200 may be used for processing and analysis of imaging data provided by the OCT system 100. In some cases, the computing module 200 may operate as a control system or controller, and in other cases, may be connected to a separate control system or controller. Further, the computing module 200 may host a user-accessible platform for invoking services, such as reporting and analysis services, and for providing computational resources to effect machine learning techniques on the imaging data.

Figure 2:
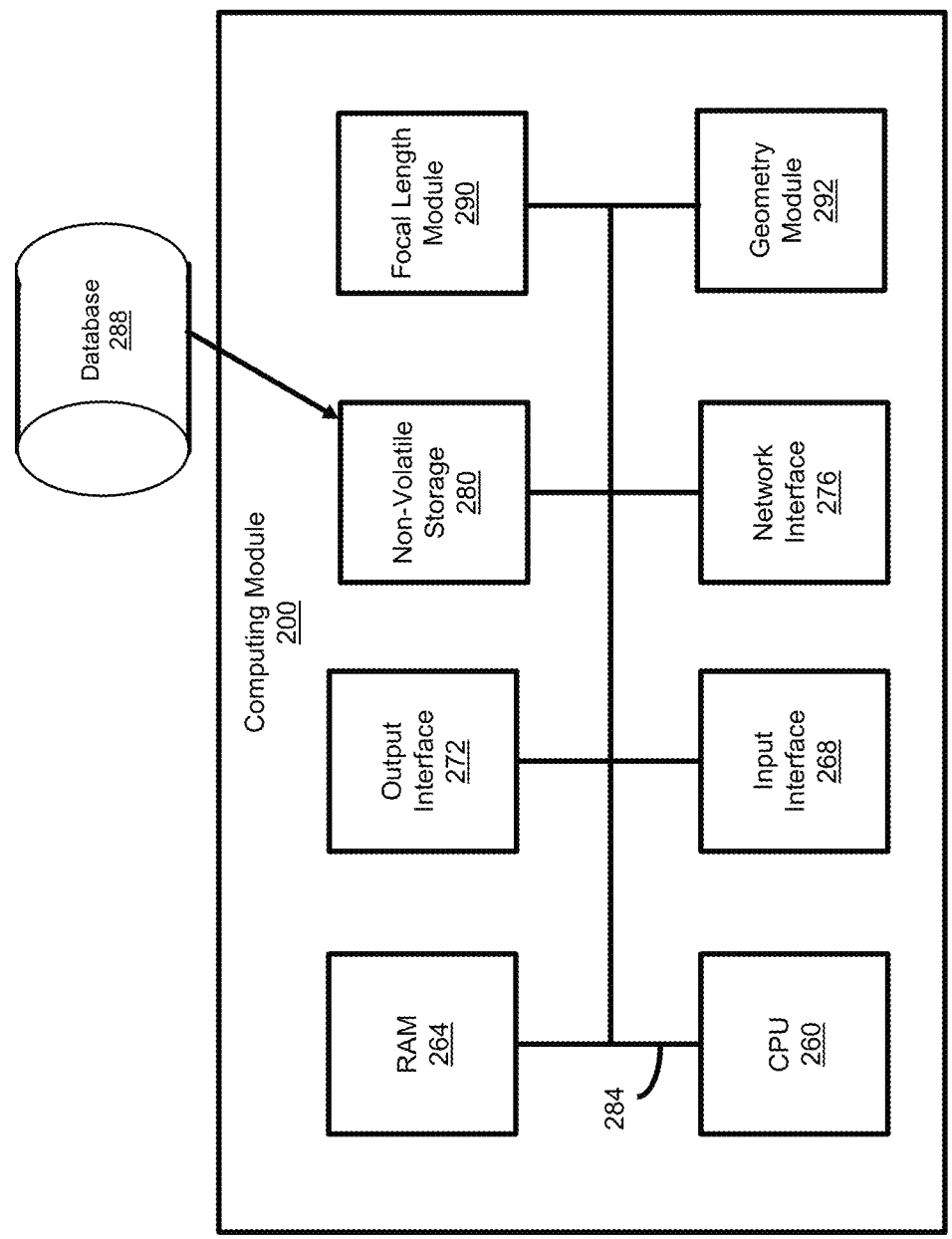
FIG. 2 is a schematic diagram for a computing module, according to the system of FIG. 1.

In an embodiment, as shown in FIG. 2, the computing module 200 can include a number of physical and logical components, including a central processing unit ("CPU") 260, random access memory ("RAM") 264, an input interface 268, an output interface 272, a network interface 276, non-volatile storage 280, and a local bus 284 enabling CPU 260 to communicate with the other components. CPU 260 can include one or more processors. RAM 264 provides relatively responsive volatile storage to CPU 260. The input interface 268 enables an administrator to provide input via, for example, a keyboard and mouse. The output interface 272 outputs information to output devices, for example, a display or speakers. The network interface 276 permits communication with other systems or computing devices. Non-volatile storage 280 stores the operating system and programs, including computer-executable instructions for implementing the OCT system 100 or analyzing data from the OCT system 100, as well as any derivative or related data. In some cases, this data can be stored in a database 288. During operation of the system 200, the operating system, the programs and the data may be retrieved from the non-volatile storage 280 and placed in RAM 264 to facilitate execution. In an embodiment, the CPU 260 can be configured to execute various modules, for example, a depth-of-field module 290 and a geometry module 292.

In some cases, the system 100 can use machine learning (ML) to transform raw data from the A-scan, B-scan, or C-scan into a descriptor. The descriptor is information associated with a particular defect in the object. The descriptor can then be used to determine a classifier for the defect. As an example, the CPU 260 can do this detection and classification with auto-encoders as part of a deep belief network.

OCT systems 100 generally use different localization techniques to obtain information in the axial direction, along the axis of the originating optical beam 112 (z-axis), and obtain information in the transverse direction, along a plane perpendicular to the axis of the originating beam 112 (x-y axes). Information gained from the axial direction can be determined by estimating the time delay of the optical beam reflected from structures or layers associated with the object 108. OCT systems 100 can indirectly measure the time delay of the optical beam using low-coherence interferometry.

Typically, OCT systems that employ low-coherence interferometry can use an optical source 102 that produces an optical beam 112 with a broad optical bandwidth. The originating optical beam 112 coming out of the source 102 can be split by the beam splitter 110 into two derivative beams (or paths). The first derivative beam 114 can be referred to as the reference beam (or path or arm) and the second derivative beam 120 can be referred to as the sample beam (or path or arm) of the interferometer. Each derivative beam 114, 120 is reflected back and combined at the detector 106.

The detector 106 can detect an interference effect (fast modulations in intensity) if the time travelled by each derivative beam in the reference arm and sample arm are approximately equal; whereby "equal" generally means a difference of less than a 'coherence length.' Thus, the presence of interference serves as a relative measure of distance travelled by light on the sample arm.

For OCT, the reference arm can be scanned in a controlled manner, and the reference beam 114 can be recorded at the detector 106. An interference pattern can be detected when the mirror 104 is nearly equidistant to one of the reflecting structures or layers associated with the object 108. The detected distance between two locations where the interference occurs corresponds to the optical distance between two reflecting structures or layers of the object in the path of the beam. Advantageously, even though the optical beam can pass through different structures or layers in the object, OCT can be used to separate out the amount of reflections from individual structures or layers in the path of the optical beam.

With respect to obtaining information in the transverse direction, as described below, the sample beam 120 can be focused on a small area of the object 108, potentially on the order of a few microns, and successively scanned over a region of the object 108.

In an embodiment of an OCT system, Fourier-domain can be used as a potentially efficient approach for implementation of low-coherence interferometry. Instead of recording intensity at different locations of the reference reflective element 104, intensity can be detected as a function of wavelengths or frequencies of the optical beam 112. In this case, intensity modulations, as a function of frequency, are referred to as spectral interference. Whereby, a rate of variation of intensity over different frequencies can be indicative of a location of the different reflecting structures or layers associated with the object. A Fourier transform of spectral interference information can then be used to provide information similar to information obtained from scanning of the reflective element 104.

In an embodiment of an OCT system, spectral interference can be obtained using either, or both, of spectral-domain techniques and swept-source techniques. With the spectral-domain technique, the optical beam can be split into different wavelengths and detected by the detector 106 using spectrometry. In the swept-source technique, the optical beam produced by the optical source 102 can sweep through a range of optical wavelengths, with a temporal output of the detector 106 being converted to spectral interference.

Advantageously, employing Fourier-domain can allow for faster imaging because back reflections from the object can be measured simultaneously.

The resolution of the axial and transverse information can be considered independent. Axial resolution is generally related to the bandwidth, or the coherence-length, of the originating beam 112. In the case of a Gaussian spectrum, the axial resolution ($\Delta z$) can be: $\Delta z = 0.44 * \lambda_0^2 / \Delta \lambda$, where $\lambda_0$ is the central wavelength of the optical beam and $\Delta \lambda$ is the bandwidth defined as full-width-half-maximum of the originating beam. In other cases, for spectrum of arbitrary shape, the axial spread function can be estimated as required.

In some cases, the depth of the topography imaging for an OCT system is typically limited by the depth of penetration of the optical beam into the object 108, and in some cases, by the finite number of pixels and optical resolution of the spectrometer associated with the detector 106. Generally, total length or maximum imaging depth $z_{max}$ is determined by the full spectral bandwidth $\lambda_{full}$ of the spectrometer and is expressed by $z_{max} = (1/4N) * (\lambda_0^2 / \lambda_{full})$ where N is the total number of pixels of the spectrometer.

With OCT systems, sensitivity is generally dependent on the distance, and thus delay, of reflection. Sensitivity is generally related to depth by: $R(z) = \sin(p*z)/(p*z) * \exp(-z^2/(w*p))$. Where w depends on the optical resolution of spectrometer associated with the detector 106. The first term related to the finite pixels in the spectrometer and the second term related to the finite optical resolution of the spectrometer.

When implementing the OCT system 100, reflected sample and reference optical beams that are outside of the coherence length will theoretically not interfere. This reflectivity profile, called an A-scan, contains information about the spatial dimensions, layers and location of structures within the object 108 of varying axial-depths; where the 'axial' direction is along the axis of the optical beam path. A cross-sectional tomograph, called a B-scan, may be achieved by laterally combining a series of adjacent A-scans along an axis orthogonal to the axial direction. A B-scan can be considered a slice of the volume being imaged. One can then further combine a series of adjacent B-scans to form a volume which is called a C-scan. Once an imaging volume has been so composed, a tomograph, or slice, can be computed along any arbitrary plane in the volume.

A-scans represent an intensity profile of the object, and its values (or profile) characterize reflectance of the way the optical beam penetrates the surface of the object. Thus, such scans can be used to characterize the material from the surface of the object to some depth, at an approximately single region of the object 108. As used in the present disclosure, the term 'surface', of an object, is understood to include the peripheral surface down to the depth of penetration of the A-scan. B-scans can be used to provide material characterization from the surface of the object 108 to some depth, across a contour on the surface of the object 108.

The system 100, as described herein, can be used to detect features associated with the surface and subsurface of an object; and in some cases, for later categorization of such features. In a particular case, such features are defects in the object, due to, for example, various manufacturing-related errors or conditions.

In some cases, the depth-of-field adjusting mechanism 125 can be, for example, a focus-tuneable lens. In a particular example, the focus-tuneable lens can be a liquid lens. With liquid lenses, each lens is filled with an optical liquid. When a user or system applies a voltage, the change in voltage alters the pressure profile of the liquid, resulting in a change in radius of curvature to each lens. This change in radius causes the lens to change the effective depth of field of the sample beam 120, for example, in the range of +15 to +120 mm using an aperture of 10 mm. In further cases, the depth-of-field adjusting mechanism 125 can be two or more lens that are mechanically translated relative to each other, thereby changing the effective depth of field of the sample beam 120.

Figure 6:
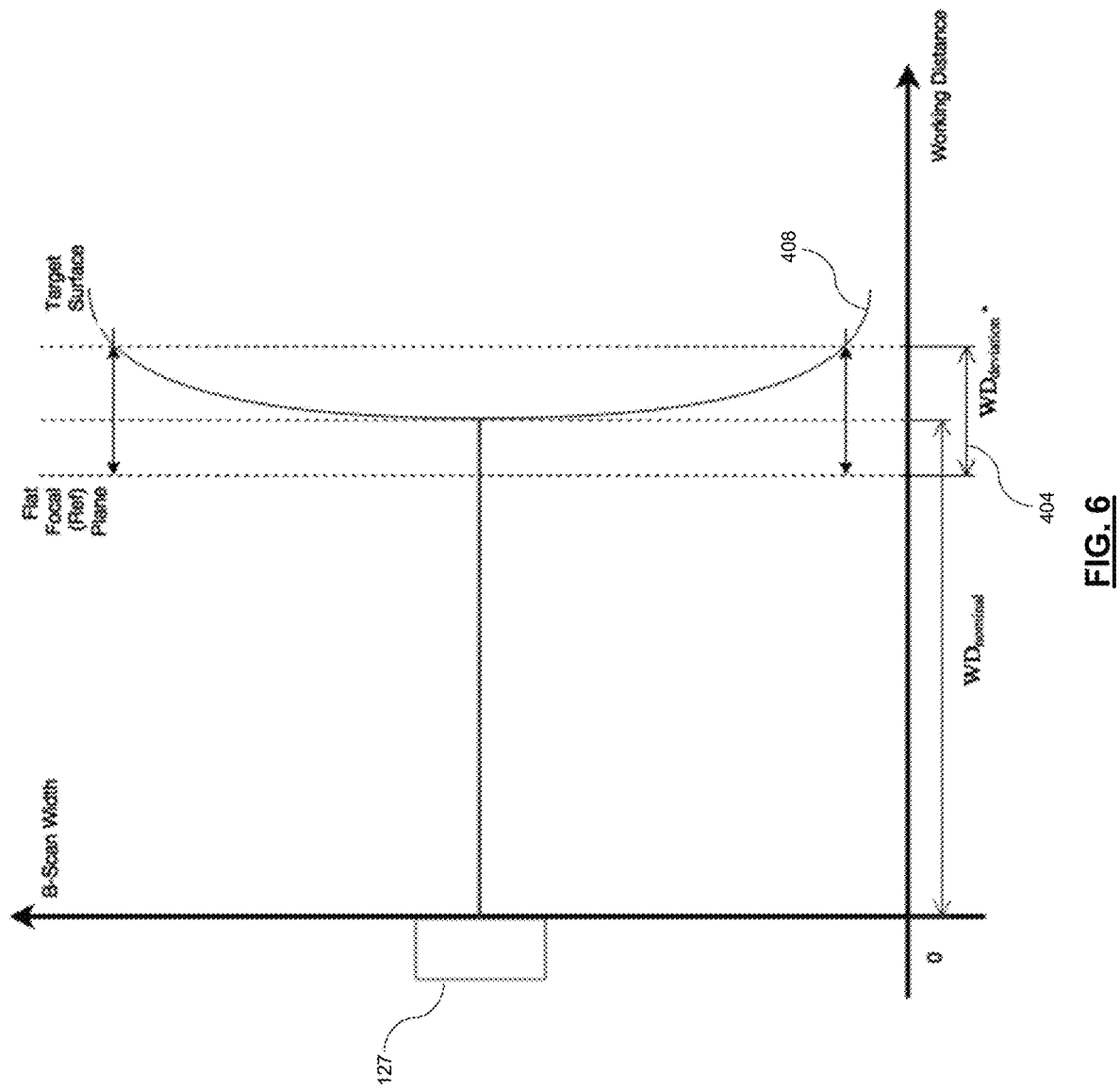
FIG. 6 is a diagrammatic side view of a scanner head and object, according to the system of FIG. 1.

In many circumstances, the object to be scanned by the OCT system 100 is not flat and can have a curved or otherwise modulating surface or profile. FIGS. 4A and 4B show a portion of an object 408 having a curved surface to be scanned; and in some cases, the curved surface may be considered monotonic. FIG. 4A illustrates a scanner head 121 scanning the object 408 at a first instance of time and FIG. 4B shows such scanner head 121 scanning the object 408 at a later instance of time. In this case, the object 408 is moved in the direction illustrated by arrow 407 relative to the fixed scanner head 121. The scanner head 121 is directed at the object 408 and includes the depth-of-field adjusting mechanism 125. A present working distance ("WD") 402 is illustrated as the distance between the scanner head 121 or the depth-of-field adjusting mechanism 125 and the surface of the object 408. A present depth of field 404 (or "confocal parameter" if the beam is assumed to be Gaussian) is also illustrated and represents the distance over which the surface of the object 408 is in focus during the A-scan. Depth of field, as used herein, is understood to be a distance about a plane of focus (POF) in which objects in an image appear sufficiently sharp, and thus, the objects are in focus. In some cases, as exemplified in greater detail in FIG. 6, the upper boundary of the depth of field 404, being the boundary closest to the scanner head 121, can be called a focal reference plane. The lower boundary of the depth of field 404, being the boundary farthest from the scanner head 121, can be called the working distance deviation.

As shown in FIG. 4B, as the object is moved along its direction of travel, the working distance 402 can increase or decrease due to the modulations in the profile of the object 408; in this case, the working distance 402 increased as the surface became further away from the scanner head 121 along the axial direction. As shown in FIG. 4B, the increase was such that the depth of field 404 no longer includes the surface of the object 408 within operational focus.

One approach to resolve the above problem is to adjust the path length of the reference arm 114. In an example, this can include having the reflective element 104 on a motorized mechanism that translates the mirror along the axial direction of the reference beam 114 in order to shorten or lengthen the path length. In another example, this can include incorporating a liquid lens in the reference path 114 in order to change the effective reference path length. However, adjusting the path length may be inadequate for applications where the object is moving relative to the scanner head, due to computational and speed concerns.

Figure 5:
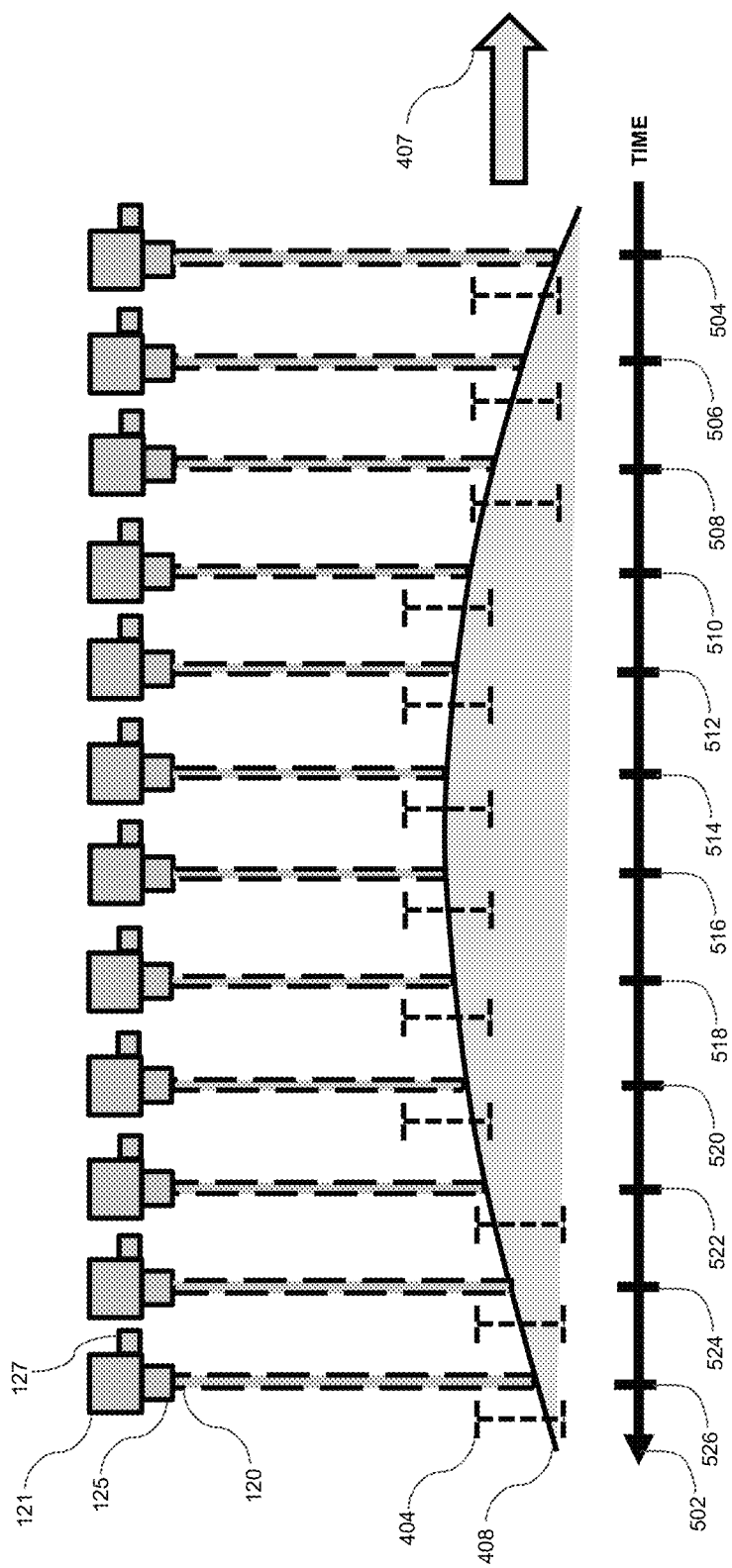
FIG. 5 is a diagrammatic side view of a scanner head and object over time, according to the system of FIG. 1.

In the present embodiments, the system 100 can use the depth-of-field adjusting mechanism 125 to change the depth of field of the sample beam 120 to adjust for the changes in the profile of the surface of the object 408. As shown in FIG. 5, the depth-of-field adjusting mechanism 125 changes the depth of field over time as the object 408 passes by the scanner head. FIG. 5 illustrates successive positions, over time, of the object 408 as it moves in direction 407 relative to the fixed scanner head 121. For reference, a time scale 502 is illustrated with demarcations 504 to 526 each representing divisions of time. As illustrated, the depth of field 408 is adjusted by the depth-of-field adjusting mechanism 125 in order to ensure that the surface of the object 408 is within the depth of field.

Figure 3:
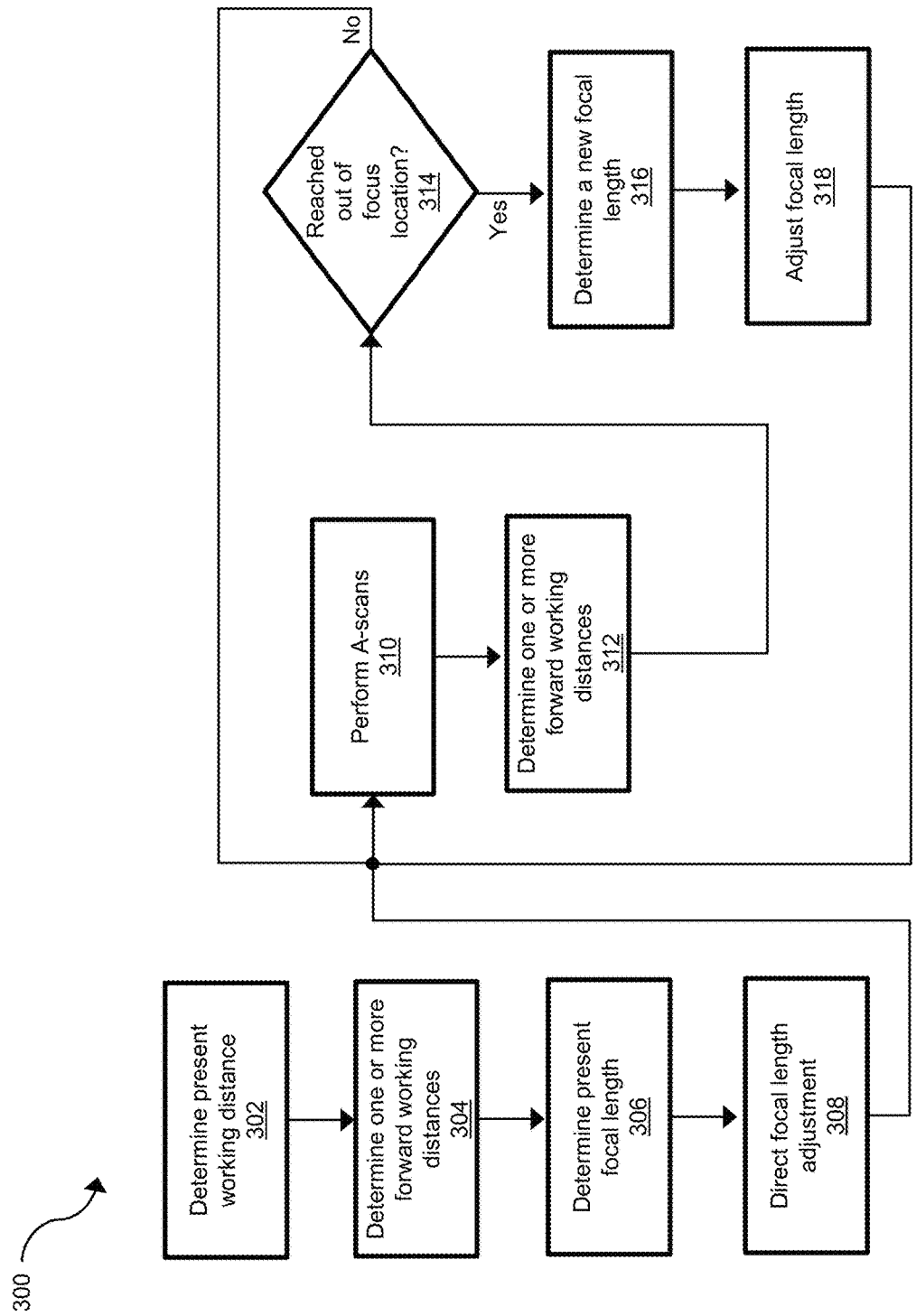
FIG. 3 is a flowchart for a method for surface inspection of an object using optical coherence tomography (OCT), according to an embodiment.

Referring now to FIG. 3, shown therein is a method 300 of surface inspection using the OCT system 100, in accordance with an embodiment. The method 300 may be used for inspecting the surface of an object 408 when the object 408 is moved relative to the scanner head 121. In an exemplary case, the method can be for the purposes of detecting surface defects or irregularities. In this embodiment, the system 100 can determine the working distance at some distance ahead of the scanner head 121, along the axis of movement of the object 408. This determination can be via either having the distance determination module 127 at a predetermined distance ahead of the scanner head 121, by having one or more additional distance determination modules 127 at a predetermined distance ahead of the scanner head 121, or via determining the working distance from the surface geometry at a predetermined distance ahead of the scanner head 121 by the geometry module 292, or a combination of the above. In some cases, the distance determination module 127 can comprise the geometry module 292 or perform its functions. In this way, the system 100 can anticipate upcoming changes in the surface profile of the object 408 and adjust the depth of field accordingly.

At block 302, the system 100 determines a present working distance, being the distance from the scanner head 121 to the surface of the object 408, for example, with the distance determination module 127. At block 304, the system 100 determines one or more forward working distances, for example, with the distance determination module 127. The one or more forward working distances are each determined at a location that is at a distance in front of the present working distance opposite the direction of travel 407 of the object 408. As an example, in FIG. 5, if the present working distance is determined at the location demarcated by time division 504, then one of the forward working distances can be determined at the location demarcated by time division 506 and another one of the forward working distances can be determined at the location demarcated by time division 508.

At block 306, the depth-of-field module 290 determines a present depth of field that has the object's 408 surface in focus at the present working distance and, to the extent possible, at as many successively adjacent forward working distances for which working distances have been determined in 304. As an example, in FIG. 5, determining a depth of field that has the surface of the object 408 in focus at the location demarcated by time division 504, then at the location demarcated by time division 506, then at the location demarcated by time division 508, then at the location demarcated by time division 510, and so on. As shown in FIG. 5, the depth-of-field module 290 can determine a depth of field that has the object's 408 surface in focus at the locations demarcated by time divisions 504, 506 and 508; but not at the location demarcated by time division 510 because the surface would be outside of the depth of field common to the locations demarcated by time divisions 504, 506 and 508.

At block 308, the CPU 260 directs the depth-of-field adjusting mechanism 125 to adjust the current depth of field to the determined present depth of field 404.

At block 310, the system 100 performs successive A-scans of the object 408, as described herein, at the location of the present working distance, and then at the location of each of the forward working distances determined to be within the present depth of field as the object 404 is moved by the object translator 109.

At 312, as time progresses and the object 404 is moved by the object translator 109, the system 100 continues determining one or more forward working distances ahead of the location presently scanned. At 314, when the CPU 260 determines that the scanner head 121 has reached a present working distance at a present location having the object's surface not in the depth of field, then at 316, the depth-of-field module 290 determines a present depth of field that has the object's 408 surface in focus at the present working distance and, to the extent possible, at as many successively adjacent forward working distances for which working distances have been determined in 312. At block 318, the CPU 260 directs the depth-of-field adjusting mechanism 125 to adjust the current depth of field to the determined new depth of field.

The system 100 repeats blocks 310 to 318 for successive divisions of time as the object is moved along by the object translator 109. These successive A-scans can be aggregated by the computing module 200. The aggregation technique may involve stacking images comprising the imaging data according to image processing techniques. In an embodiment, aggregation of imaging data may include the formation of a B-scan from a plurality of A-scans. In some cases, the B-scan and/or A-scans are presented to a user via the output interface 272.

The method 300 has the intended advantage of effectively 'looking ahead' such that the depth of field is adjusted to anticipate upcoming changes in the profile of the object. In this way, the depth of field requires less adjustment and, in some cases, allows the system 100 to complete a B-scan more quickly, or allows a B-scan to comprise more A-scans when the object is moving at a fixed rate.

In method 300, it is generally understood that the surface of the object 408 being within the boundaries of the depth of field 404 includes approximately the totality of the A-scan axial depth being within the boundaries of the depth of field 404.

Advantageously, the approach described herein does not require that the depth of field be changed for every A-scan or every set of A-scans, which can be slow, especially for applications where the object 408 is moving relative to the scanner head 121. Rather, the approach described herein advantageously only requires a change in depth of field when necessitated by the profile of the object 408.

In some embodiments, the working distance can be determined by analysis of the A-scan to determine if the object 408 is within the depth of field 404. However, this approach is limited in speed and responsiveness due to having to analyze the A-scan and then having to retake the A-scan if it is not in focus. Advantageously, the method 300 measures the working distance prior to the A-scan, such that it is faster and more efficient, and is able to scan an object 408 in movement.

Figure 7:
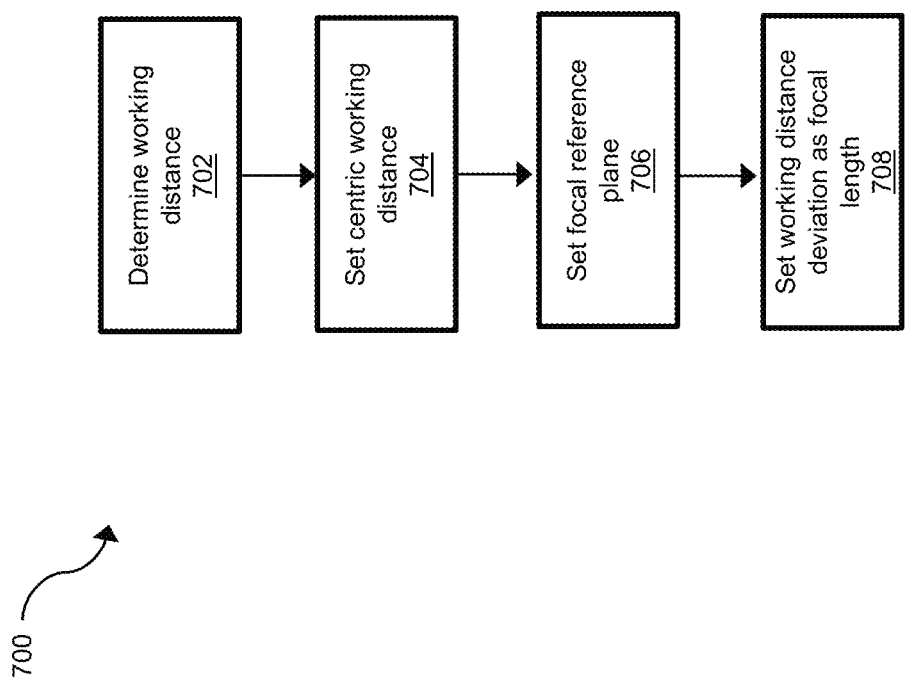
FIG. 7 is a method for determining depth of field, according to another embodiment.

In a particular embodiment of method 300, as shown in FIG. 7, the depth of field 404 can be initially determined, prior to considering the forward working distances, at block 306 and/or block 316, by method 700. At block 702, the working distance is determined by the distance determination module, being the distance from the scanner head 121 to the surface of the object 408. At block 704, the distance determination module sets the determined distance as a "centric working distance". At block 706, the distance determination module subtracts half of the value of the A-scan depth of field 404 from the centric working distance and sets this result as the "focal reference plane", as defined above. At block 708, the distance determination module sets the "working distance deviation", as defined above, below the focal reference plane as the depth of field 404.

Figure 8:
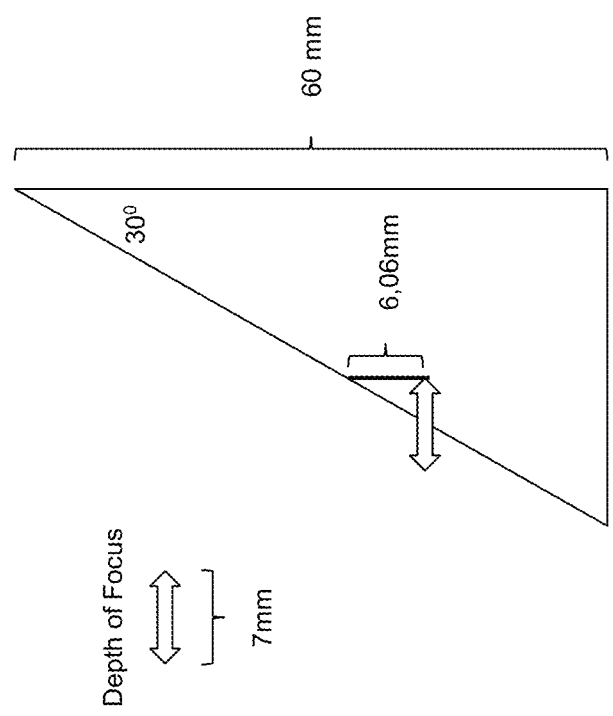
FIG. 8 is an illustration of depth of field.

As an example of the embodiments described herein, as shown in FIG. 8, there is an optical setup with 7 mm of depth of field, with an object having an inclined surface at 30° inclination. With this configuration, the depth of field would have to be changed approximately ten times (meaning there are ten focus quantization levels) in order to have the inclined target in focus. While the object is moved in relation to the scanner head, the focus would be shifting over such time. Advantageously, the depth of field 404 can be effectively used as a low pass filter decreasing the speed and diopters that the focus needs to be adjusted in a single B-scan.

While in the present embodiments the object is described as 'moving' via the object translator 109, it is appreciated that moving can include successively moving and stopping the object 108 for scanning, or can include continuously moving the object. Additionally, while in the present embodiments, the movement is shown along a single dimensional axis, it is appreciated that the movement of the object can be along a two-dimensional plane.

In some embodiments, the depth-of-field adjusting mechanism 125 may not capable of adjusting the depth of field quickly enough for each A-scan. In this case, the system 100 can take an A-scan at the appropriate speed of the depth-of-field adjusting mechanism 125 and use digital signal processing or machine learning techniques to fill in for the missing intermediate A-scans in the aggregated B-scan.

In some cases, after the A-scans, B-scans, and/or C-scans have been determined, the system can detect whether there are defects in the object using image interpretation and machine learning techniques. The defective label indicates that an unacceptable defect has been detected, and in some cases, such defect is of a particular type. In the example where the object is a vehicle part, the defect may have different shapes and dimensions. As an example, the defect may be an unwanted round seed or crater, or the like, on or under the surface of the part. As another example, the defect may have an elongated shape, such as with an unwanted fiber, or the like, on or under the surface of the part. As an example, the acceptable/defective label may be with regards to the size, area, or volume of a defect. In another example, acceptable/defective label may be with regards to the presence of defect between different layers of films applied in an industrial process; for example, in an automotive setting, in an electro-deposition (ED) layer, a colour layer, or a clear layer, where each layer is in the order of tens of microns thick.

In some cases, based on analysis of the OCT images, the system 100 can provide further information in the form of feature localization on the object. As an example, the information may be that there is fiber defect at location x=3.4 cm, y=5.6 cm on a vehicle part. Feature localization can also be specified with respect to surface depth, along the z-axis. Depth localization can be particularly advantageous in certain applications; for example, when thin films are being applied to a vehicle part. In this case, for example, after a vehicle part is painted, paint inspection may be required on various layers including an electro-deposition layer, a colour layer, and a clear coat layer. Being able to detect and determine the presence of a defect between any two of these layers is particularly advantageous because it has implications on the amount of re-work that may be required to resolve the imperfection. It can also be advantageous for improvement to a manufacturing process by being able to determine what type of defect is located at what layer; for example, a faulty HVAC system in the manufacturing environment could be responsible for introducing defects between layers. In this regard, being able to localize defect origin to a portion of the manufacturing path is an advantage to reduce future defects and rework.

The machine-learning techniques described herein may be implemented by providing input data to a neural network, such as a feed-forward neural network, for generating at least one output. The neural network may have a plurality of processing nodes, including a multi-variable input layer having a plurality of input nodes, at least one hidden layer of nodes, and an output layer having at least one output node. During operation of a neural network, each of the nodes in the hidden layer applies a function and a weight to any input arriving at that node (from the input layer or from another layer of the hidden layer), and the node may provide an output to other nodes (of the hidden layer or to the output layer). The neural network may be configured to perform a regression analysis providing a continuous output, or a classification analysis to classify data. The neural networks may be trained using supervised or unsupervised learning techniques. According to a supervised learning technique, a training dataset is provided at the input layer in conjunction with a set of known output values at the output layer; for example, imaging data for which defect location and/or existence is known. During a training stage, the neural network may process the training dataset. It is intended that the neural network learn how to provide an output for new input data by generalizing the information it learns in the training stage from the training data. Training may be affected by back-propagating error to determine weights of the nodes of the hidden layers to minimize the error. The training dataset, and the other data described herein, can be stored in the database 288 or otherwise accessible to the computing module 200. Once trained, or optionally during training, test data can be provided to the neural network to provide an output. The neural network may thus cross-correlate inputs provided to the input layer in order to provide at least one output at the output layer. Preferably, the output provided by the neural network in each embodiment will be close to a desired output for a given input, such that the neural network satisfactorily processes the input data.

In some embodiments, the machine learning techniques can employ, at least in part, a long short-term memory (LSTM) machine learning approach. The LSTM neural network allows for quickly and efficiently performing group feature selections and classifications.

In some embodiments, the detection can be by employing, at least in part, a convolutional neural network (CNN) machine learning approach.

While certain machine-learning approaches are described, specifically LSTM and CNN, it is appreciated that, in some cases, other suitable machine learning approaches may be used where appropriate.

Figure 9A:
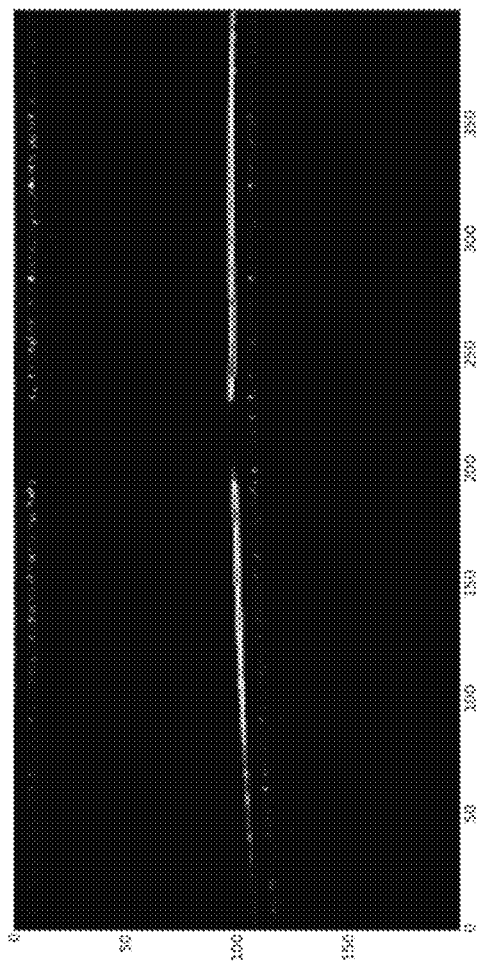
FIG. 9A is an exemplary B-scan in which a defect was detected in a paint layer of a vehicle part.
Figure 9B:
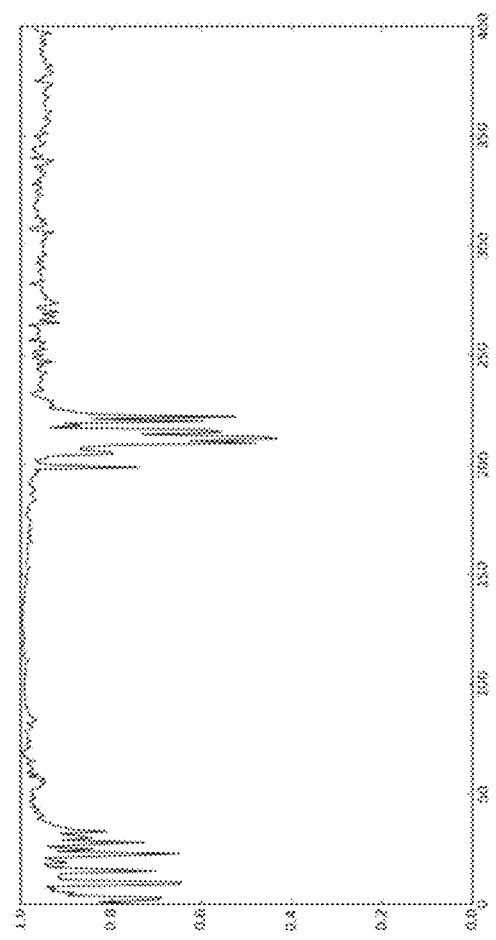
FIG. 9B is a plot of a score produced for the exemplary B-scan of FIG. 9A.

As an example, FIG. 9A illustrates an B-scan in which a defect was detected in a paint layer of a vehicle part. As shown, the defect is centered at approximately $225 \times 10^{-2}$ mm along the fast scan axis (x-axis). Correspondingly, FIG. 9B illustrates a plot of a score produced by the CPU 260, between 0 and 1, representing a determined possibility that a defect is present in the exemplary B-scan of FIG. 9A.

Figure 10A:
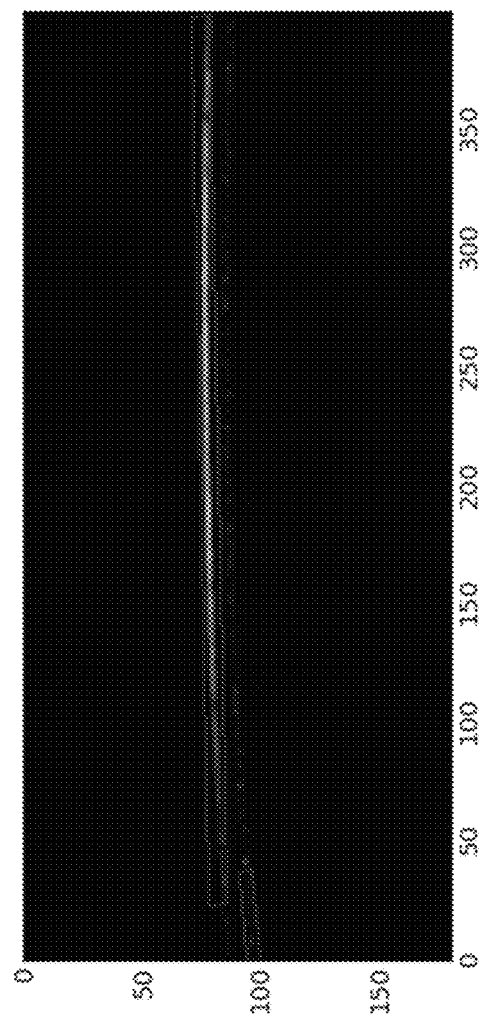
FIG. 10A is an exemplary B-scan in which the system determined there are no features present.
Figure 10B:
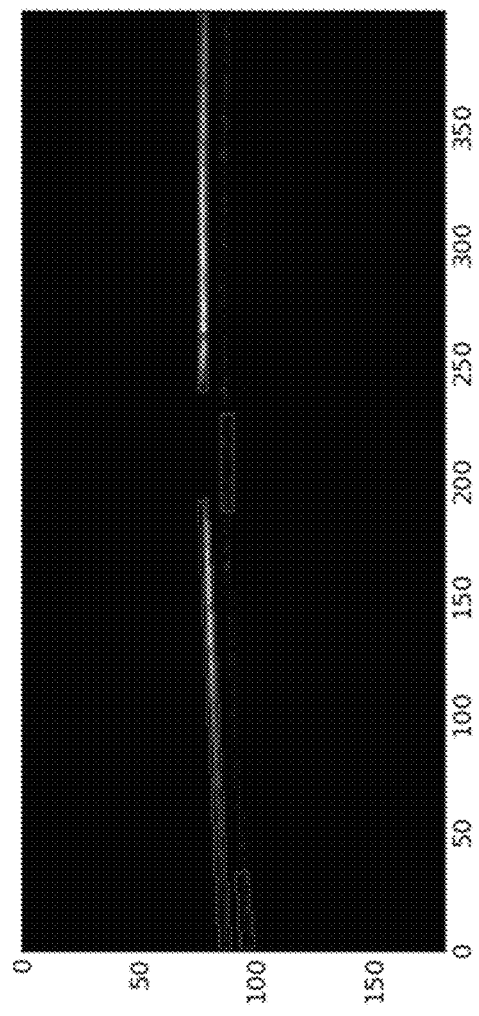
FIG. 10B is an exemplary B-scan in which the system determined there are features present.

As an example, FIG. 10A illustrates a B-scan in which contours are outlined. In this case, the CPU 260 determined that there was no defect detected on the object. FIG. 10B also illustrates a B-scan in which contours are outlined. In this case, the CPU 260 determined that there was a defect detected on the object.

Figure 11:
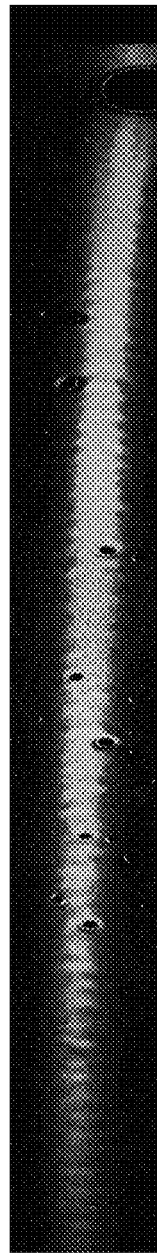
FIG. 11 is an exemplary image captured to form a top-level surface view of an object.

FIG. 11 illustrates an exemplary image captured to form a top-level surface view of an object.

Figures 12A, 12B:
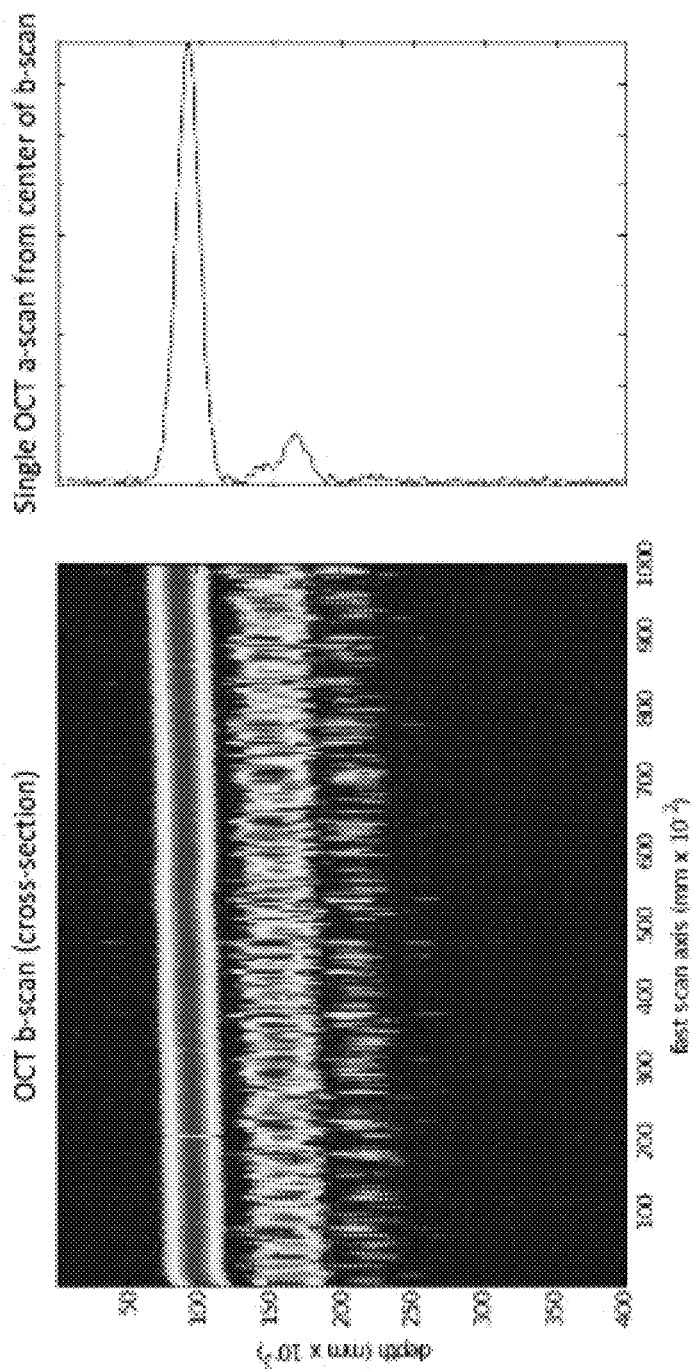
FIG. 12A is an exemplary B-scan of an object without problematic defects or features.
FIG. 12B is an exemplary A-scan of the object.

FIG. 12A illustrates an exemplary B-scan (cross-section) of an object without problematic defects or features (i.e., a 'clean' surface).

FIG. 12B illustrates an exemplary A-scan from the center of the B-scan.

Figure 13:
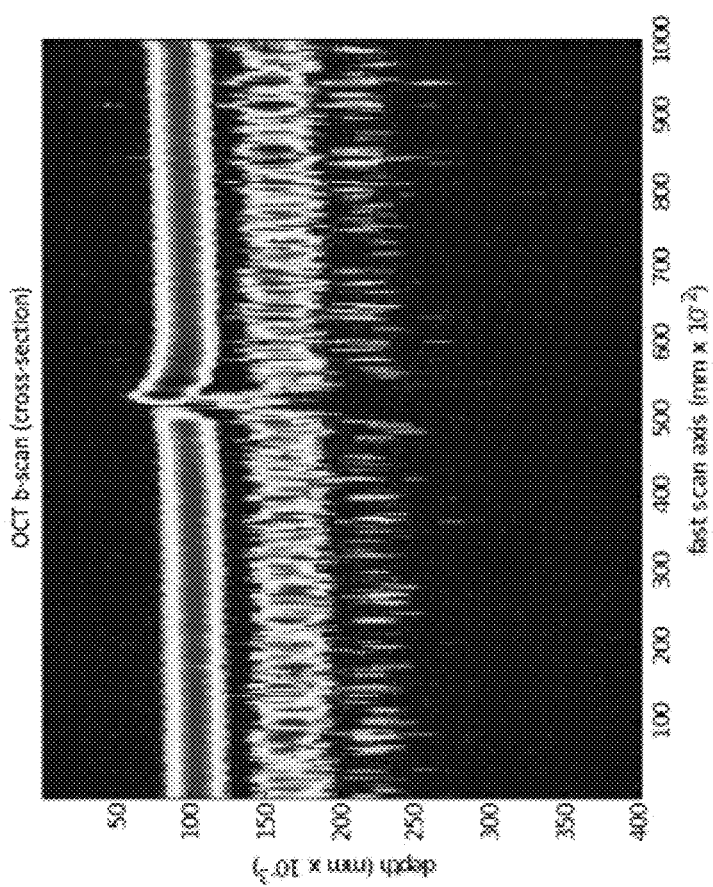
FIG. 13 is an exemplary B-scan of an object with problematic defects or features.

FIG. 13 illustrates an exemplary B-scan (cross-section) of an object with a problematic defect or feature present. In this case, as shown, there was a subsurface seed detected, centered at approximately 500 along the x-axis.

Figure 14:
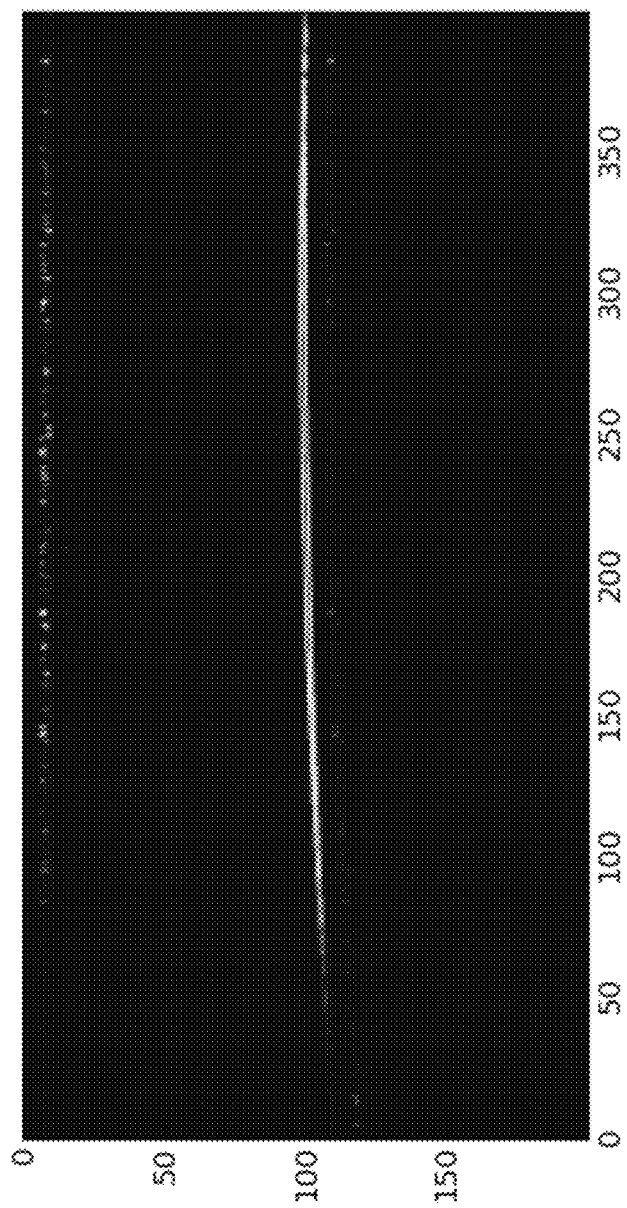
FIG. 14 is an exemplary B-scan of an object for determining whether there are defects.
Figure 15:
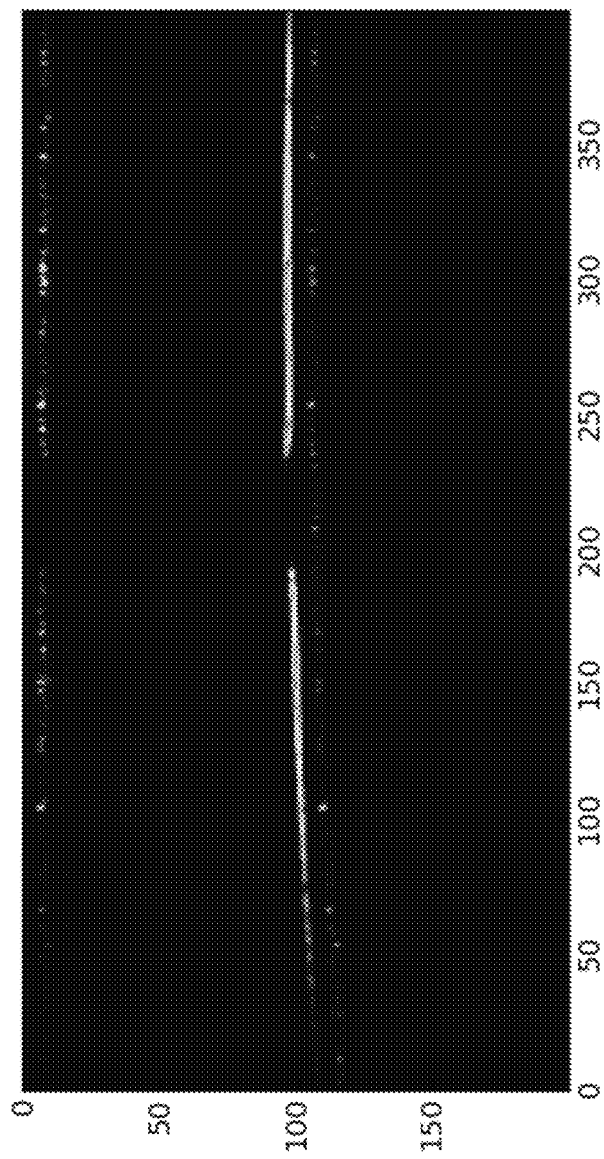
FIG. 15 is an exemplary B-scan of an object showing a defect.

FIG. 14 illustrates an exemplary B-scan of a vehicle part for determining whether there are painting defects. In this case, there was no defect from the B-scan. FIG. 15 illustrates an exemplary B-scan of a vehicle part for determining whether there are painting defects. In this case, as shown, there was a defect in the paint layer detected, centered at approximately 225 along the x-axis.

Figure 16A:
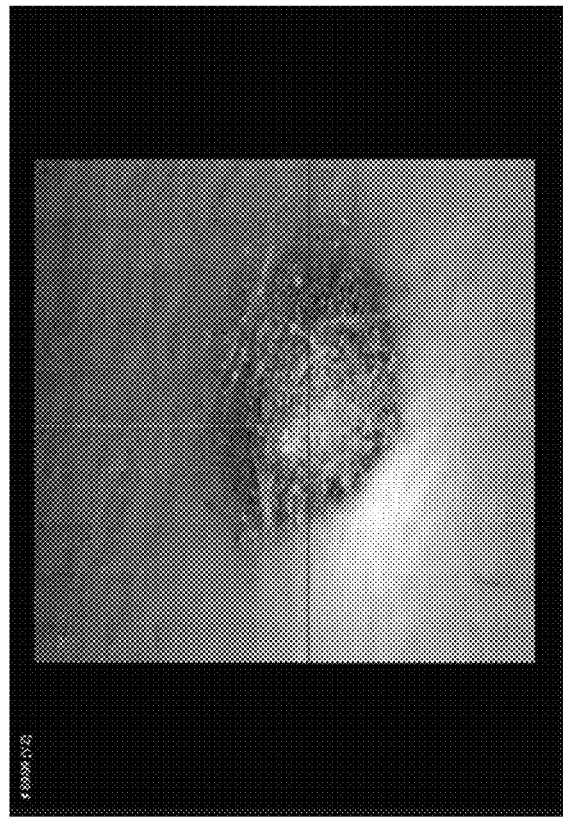
FIGS. 16A and 16B illustrate, at respectively different angles of perspective, an exemplary C-scan.
Figure 16B:
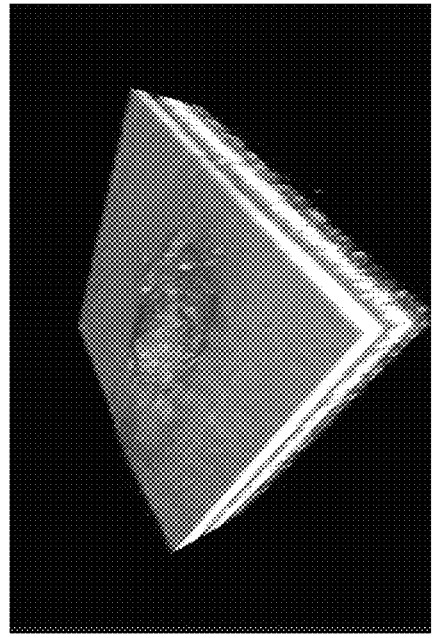

FIGS. 16A and 16B illustrate, at respectively different angles of perspective, an exemplary C-scan of a vehicle part. In this case, a seed was detected as a defect in the painting of a vehicle part.

In further embodiments, machine learning can also be used by the CPU 260 to detect and compensate for data acquisition errors at the A-scan, B-scan and C-scan levels.

The embodiments described herein include various intended advantages. As an example, instead of having to change depth of field and/or reference path length for every A-scan, the embodiments described herein allow for depth of field adjustment only when required, allowing A-scans to be completed more quickly or allowing more A-scans to be undertaken.

Although the invention has been described with reference to certain specific embodiments, various modifications thereof will be apparent to those skilled in the art without departing from the spirit and scope of the invention as outlined in the claims appended hereto. The entire disclosures of all references recited above are incorporated herein by reference.

The invention claimed is:

1. A method of surface inspection of an object using optical coherence tomography (OCT), the OCT having an associated tunable depth of field comprising a distance range, the method comprising:
   determining a present depth of field such that a series of multiple forward surface locations on the object are located within the associated distance range, wherein the multiple forward surface locations are sequentially located opposite a direction of travel of the object;
   tuning the tunable depth of field to the present depth of field; and
   performing a scan of the object at each surface location in the series of surface locations.

2. The method of claim 1, wherein the scan of the object comprises an A-scan.

3. The method of claim 2, using the A-scans data, the method further comprising detecting a feature on a surface or subsurface of the object using a neural network trained using a training set, the training set comprising A-scans data labelled with the feature.

4. The method of claim 1, wherein the scan for each of the surface locations that are sequentially located opposite the direction of travel of the object are combined to form a B-scan.

5. The method of claim 1, further comprising:
   determining a subsequent depth of field having a subsequent series of multiple forward surface locations on the object located within the associated distance range;
   tuning the tunable depth of field to the subsequent depth of field; and
   performing a scan of the object at each surface location in the subsequent series of surface locations.

6. The method of claim 5, wherein determining the present depth of field and the subsequent depth of field each comprise measuring a distance between the scanner head and each surface location of the object.

7. The method of claim 5, wherein determining the present depth of field and the subsequent depth of field each comprise determining a distance between the scanner head and each surface location of the object using surface geometry of the object.

8. A system for surface inspection of an object using optical coherence tomography (OCT), the OCT having a tunable depth of field comprising a distance range, the system for surface inspection comprising:
   a depth-of-field module to determine a present depth of field such that a series of multiple forward surface locations on the object are located within a distance range associated with the present depth of field, wherein the multiple forward surface locations are sequentially located opposite a direction of travel of the object;
   a depth-of-field adjusting mechanism to tune the tunable depth of field to the present depth of field; and
   a scanner head to perform a scan of the object at each surface location in the series of surface locations by directing optical beams towards the object and detecting optical beams returning from the object.

9. The system of claim 8, further comprising an object translator to move the object along a direction of travel.

10. The system of claim 8, wherein the scan of the object comprises an A-scan.

11. The system of claim 10, further comprising a computing module to, using the A-scan data, detect a feature on a surface or subsurface of the object using a neural network trained using a training set, the training set comprising A-scans data labelled with the feature.

12. The system of claim 8, wherein the scan for each of the surface locations that are sequentially located opposite the direction of travel of the object are combined to form a B-scan.

13. The system of claim 8, wherein the depth-of-field module further determines a subsequent depth of field having a subsequent series of multiple successive surface locations on the object located within a distance range associated with the subsequent depth of field, wherein the depth-of-field adjusting mechanism further tunes the tunable depth of field to the subsequent depth of field, and wherein the scanner head further performs a scan of the object at each surface location in the subsequent series of surface locations by directing optical beams towards the object and detecting optical beams returning from the object.

14. The system of claim 8, wherein the depth-of-field adjusting mechanism comprises a focus-tuneable lens.

15. The system of claim 14, wherein the focus-tuneable lens comprises a liquid lens.

16. The system of claim 14, wherein the focus-tuneable lens comprises two or more lenses that are mechanically translated relative to each other.

* * * * *